United States Patent [19]
Craven
[11] 4,297,339
[45] Oct. 27, 1981

[54] CONTROLLED RELEASE CYCLOHEXIMIDE COMPOSITIONS

[75] Inventor: Richard L. Craven, Kalamazoo, Mich.

[73] Assignee: The Upjohn Company, Kalamazoo, Mich.

[21] Appl. No.: 180,732

[22] Filed: Aug. 25, 1980

Related U.S. Application Data

[63] Continuation-in-part of Ser. No. 49,823, Jun. 18, 1979, abandoned.

[51] Int. Cl.[3] .................... A01N 25/26; A01N 25/34; A01N 43/40

[52] U.S. Cl. .................................. 424/19; 424/16; 424/21; 424/268; 424/274

[58] Field of Search .................... 424/16, 19, 21, 274, 424/268

[56] References Cited

U.S. PATENT DOCUMENTS

| | | | |
|---|---|---|---|
| 2,976,210 | 3/1961 | Cosby et al. | 424/16 |
| 3,092,546 | 6/1963 | Schroeter et al. | 424/16 |
| 3,813,236 | 5/1974 | Allan | 71/94 |
| 3,980,463 | 9/1976 | Meeramoto et al. | 424/224 |

OTHER PUBLICATIONS

Chem. Abst. 85-88547x (1976).
Chem. Abst. 85-29586m (1976).
Chem. Abst. 85-7077u (1976).
Merck Index 9th Ed.-(1976) p. 357, Item 2733.
Journal of the Amer. Chem. (JACS) 71, pp. 150-159 (1949).
J.A.C.S. 69-p. 474, (1947).

*Primary Examiner*—Stanley J. Friedman
*Attorney, Agent, or Firm*—John T. Reynolds

[57] ABSTRACT

Controlled release cycloheximide/emulsifier/oxidized wax compositions useful, per se, in prill form, powder form, dusts, or physically bonded to carrier particles to extend the useful fungicide life of CHI in agricultural applications.

6 Claims, No Drawings

CONTROLLED RELEASE CYCLOHEXIMIDE COMPOSITIONS

CROSS REFERENCE

This is a continuation-in-part of application Ser. No. 049,823, filed June 18, 1979, now abandoned.

DESCRIPTION

INTRODUCTION

This invention relates to agriculturally useful compositions of cycloheximide. More particularly, this invention provides new and improved control release cycloheximide compositions which broaden its potential usefulness in agricultural application.

BACKGROUND OF THE INVENTION

Cycloheximide, $C_{15}H_{23}NO_4$, beta-[2-(3,5-dimethyl-2-oxocyclohexyl)-2-hydroxyethyl]glutarimide, is now a well-known fungicide. Whiffen, et al., U.S. Pat. No. 2,574,519, issued in 1951, describes it and claims a process for its production. Cycloheximide is water soluble, active at very low concentrations against a variety of agriculturally significant fungus organisms, and is not stable in basic media or in combination with a variety of other agriculturally active components. Numerous patents have issued in the United States and elsewhere and publications are prevalent describing and claiming various ideas and attempts to stabilize cycloheximide or to prepare derivatives of cycloheximide so that its useful life could be extended for broader fungicide applications.

A few representative United States patents evidencing that type of prior art work include:

| | |
|---|---|
| Klomparens/Vellaire | U.S. 2,871,155 |
| Murray | U.S. 2,894,872 |
| Murray | U.S. 2,894,871 |
| Vellaire | U.S. 3,014,840 and |
| Schroeter/Bojack | U.S. 3,092,546 |

and others listed in an accompanying prior art statement. However, this invention is not concerned directly with stabilization of cycloheximide, but rather is directed toward providing a controlled release form of cycloheximide which extends the field life of cycloheximide as a useful fungicide where cycloheximide would be useful for combatting fungi in farm crop areas, in the presence or absence of agriculturally significant growing crops.

Prior attempts at control release of cycloheximide have included the use of cycloheximide (CHI) impregnated clay granules coated with hydrophobic materials. Such formulations do not provide adequate control of CHI, possibly due to an incomplete coat of the CHI-impregnated granule. The incompleteness or non-uniformity of the hydrophobic coating could be affected by air temperature, air movement, humidity, spray time, blender efficiency of the coating equipment, or to the lack of personnel expertise. Other attempts at controlled release of active ingredients have included the mixing of active materials, including aspirin, drugs, ascorbic acid with polyethylene glycol of 6000–7500 molecular weight range in a chlorinated, non-polar solvent, and then removing the chlorinated, non-polar solvent, e.g., by evaporation. See Gakenheimer U.S. Pat. No. 2,540,253 and DeLange, et al., U.S. Pat. No. 3,679,797. Such methods and compositions require providing equipment for the removal and recovery of huge quantities of organic solvent.

Prior patents such as U.S. Pat. No. 2,977,282 have suggested mixing plant disease antibiotics, including CHI, as aqueous solutions of antibiotics with polyhydroxy alcohols to increase the rate of absorption of the antibiotic, e.g., CHI, by the plant, thereby hopefully reducing chances of fungus disease. However, such compositions involve the use of aqueous solutions which are disadvantageous for the stable, controlled release use of CHI.

Allan, U.S. Pat. No. 3,813,236 discloses sustained release pesticide compositions involving the chemical combination of the active pesticide with an inert natural polymer (wood derivatives) such as lignin or lignin containing material such as tree bark. When exposed to environmental conditions, the chemical bond between the natural polymer and pesticide is broken by hydrolysis to yield the pesticide over an extended period of time. However, with CHI, it is preferred to avoid chemical reaction of the active ingredient, CHI, with diluents, coating agents, and carriers with which it is combined, because CHI is inherently somewhat unstable in the presence of other reactive materials. Moreover, cycloheximide has already been combined with solubilized lignin to reduce its phytotoxicity (See Klomparens, et al., U.S. Pat. No. 2,871,155), but broader and different, non-liquid methods are sought for the controlled release of CHI.

Also, Muramata, et al., U.S. Pat. No. 3,980,463 discloses a process for making granular compositions of specific size distribution range by adding solutions of active ingredients and a binder to a carrier of defined size ranges. The binder can be materials such as lignin sulfonate, carboxymethyl cellulose, polyvinyl alcohol, starch, sodium alginate, an acrylic resin, rosin, a coumarone resin, a petroleum resin, shellac and gelatin, and are dispersed in aqueous or organic liquid solvents. However, such compositions involve the use of liquid solvents which must be removed from the granular product by evaporation or otherwise.

However, by this invention there is provided an inexpensive way to provide controlled release of a water-soluble agricultural drug, CHI, which, to our knowledge, has not been done before or at least has not been published. The purpose and objects of this invention are to provide a controlled release form of CHI which is triggered by moisture over a wide range of environmental (moisture) conditions. The controlled release system of this invention will accommodate a range of CHI release rates, varying from a few minutes to several weeks. This CHI controlled release system is adaptable for adjustment to provide varying CHI release rates for many different agricultural and rodent repellant types of applications, with small or large carrier granule sizes, and this system can be applied to any fungus-susceptible surface than can be sprayed, coated, dipped, mixed with the controlled release compositions.

In summary, it is an object of this invention to provide inexpensive, controlled release compositions of CHI which are adaptable for use in a variety of application uses and which are triggered by environmental moisture to provide CHI as needed in particular applications.

Other objects and advantages of this invention will be apparent to a person in the art from the remaining specification and the appended claims.

SUMMARY OF THE INVENTION

Briefly, this invention provides a controlled release composition for CHI, which enables the preparer of the composition to provide CHI compositions which withstand the rigors of manufacturing temperature and time while still providing a variety of desired release rates for the CHI therein. Such compositions comprise (a) a hardened, substantially uniform mixture of cycloheximide, (b) an emulsifier having an HLB number of from about 5 to 18, and (c) a major amount of an oxidized wax. This above composition can also be sprayed in the liquid melt state on to inert carrier granules and then cooled to provide a solid, dispersible, granular form of CHI. These compositions can also be spray formed as prills, powders, and dusts.

DETAILED DESCRIPTION OF THE INVENTION

More specifically, this invention provides a composition useful for the controlled release application of cycloheximide which comprises a hardened, substantially uniform mixture of:

(a) from about 0.03 to 30 percent, by weight, of cycloheximide;

(b) from about 0.01 to about 25 percent, by weight, of a water-dispersible, nonionic, anionic or cationic emulsifier having an HLB (hydrophilic lipophilic balance) number within the range of from 5 to 18, preferably from 6.7 to 17, and more preferably from about 13.5 to about 15.3; and (c) from about 45 to about 99 percent by weight of an oxidized wax which contains from about 5 to about 17 pounds of oxygen per 100 pounds of wax. Such compositions can be diluted (to reduce the cost thereof) with inert diluents such as agricultural grade starch materials to the extent of about 30 percent by weight.

The cycloheximide content in the compositions can be influenced by whether the CHI/emulsifier/wax composition is to be applied directly to a growing crop for relatively fast release to the soil and plant surfaces (in which case the CHI content will be held low, usually less than one percent by weight) or whether it is intended to further apply the liquid melted CHI/emulsifier/wax composition to an inert carrier for incorporation with a granular carrier (in which case the CHI content of the liquid melted wax composition may range up to 20 to 30 percent by weight of the CHI/emulsifier/wax composition.

The oxidized wax materials used in the controlled release compositions of this invention should have a melting point higher than about 70° C. (158° F.) and lower than the temperature at which cycloheximide or the emulsifier would be decomposed therein, say, below 120° C. Good examples of useful oxidized waxes which can be used are those having melting points ranging from about 85° to 110° C. (about 190°-225° F.). The waxes can have acid numbers ranging from 5 to 50 and saponification numbers of from about 15 to 85, as those terms are defined in the wax composition art. The oxidized wax can be from any convenient source so along as it provides a hard but not brittle surface to a prill thereof at room temperature. Oxidized waxes from bees, vegetables, paraffin, hydrocarbon polymers of selected petroleum stocks as well as ethylene homopolymers and copolymers having average molecular weights of from about 500 to about 10,000 thereof, as described for example in U.S. Pat. No. 2,976,210, and the patents referred to therein, all of which are incorporated herein by reference thereto. The oxygen content of oxidized wax component can be from about 5 to about 17 pounds of oxygen per 100 pounds of wax substrate. Examples of brand-name oxidized waxes included for use in this invention include "Petronauba® C", brand of emulsifiable wax, a product of Bareco Division of the Petrolite Corporation, and said to have a melting point of 190°-200° F., an acid number of 22-28, and a saponification number of 50-60, believed to be derived from an oxidation of high molecular weight microcrystalline wax, containing 6 (units) of oxygen per 100 (units) of wax. This wax is our preferred wax for use in this invention. Other useful waxes include the BARECO® brand of emulsifiable waxes of the Bareco Division of The Petrolile Corporation, including their CERAMER® 67, CERATHANE® 63, PETROLITE® C-23, C-36, C-400, C-7500, C-8500, C-9500, PE-100, R-50 Waxes. It is essential that the cycloheximide be stable (not decomposed by heat) and the wax be melted at a temperature slightly higher than the highest melting component of the cycloheximide/emulsifier/wax melt system for a time sufficient to form a homogeneous mixture before prilling or spraying the bath of the melt.

The emulsifier component of this CHI/emulsifier/oxidized wax composition can be any non-ionic, anionic or cationic surface active agent which is non-reactive toward CHI and which agent (surfactant) has an HLB number ranging from 5 to 18. In general, the higher the HLB number rating of the surfactant, the faster the release rate of the CHI from the CHI/emulsifier/wax composition, for a given concentration of surfactants therein. In our experimental work, we prefer to use surfactants having HLB ratings of from about 6.7 to 15.3. The best specific emulsifier which we have found is a non-ionic polyoxyethylene (20) stearyl ether surfactant sold under the brand name "Brij 78" by ICI Americas, Inc., which is said to have an HLB rating of 15.3. Other surfactants which we have used in our experimental work include "Tween 65", a polyoxyethylene (20) sorbitan tristearate (HLB of 10.5), "Tween 61", a polyoxyethylene sorbitan tristearate (HLB of 10.5), "Tween 61", a polyoxyethylene sorbitan monostearate (HLB of 9.6) and "Span 40", a sorbitan monopalmitate (HLB of 6.7) of ICI Americas, Inc. Examples of preferred cationic emulsifier that can be used include:

| | |
|---|---|
| Atlas G-2090 (ICI Americas, Inc.) polyoxyethylene fatty amine combined with polyoxyethylene sorbitololeate | (HLB = 12.5) and |
| Ethomeen C/15 (Armak Industries, Chem. Div.) ethylene oxide condensation product with primary amine, and others such as | |
| Arquod C-50 | (HLB = 13.9) |

Preferred anionic emulsifiers which can be used in these compositions are exemplified by:

| | |
|---|---|
| Casul 60 (Thompson Hayward Chemical Company) calcium alkylarylsulfonate | (HLB = 10.5) and |
| Nekal NF (GAF Corporation Chemical Products) sodium alkylnaphthalene sulfonate. | |
| Duponol QC (E.I. Dupont) | |

-continued

| |
|---|
| sodium lauryl sulfate |

for which the HLB numbers are not listed in the 1979 Annual "McCutcheon's Detergent & Emulsifiers", North American Edition, McCutcheon Division, MC Publishing Co., 175 Rock Road, Glen Rock, New Jersey 07452 USA (1979).

This invention also includes the use of mixtures of CHI/emulsifier/wax compositions separately made up so to contain different emulsifiers and concentrations thereof so that in use, per se, or as an adherent part of a clay or other inert carrier granule various parts of the composition will release their CHI content at different times as needed for a particular crop protection use. For example, different CHI/emulsifier/wax composition prills having relatively fast, intermediate and slow CHI release rates can be separately sprayed onto inert carrier granules to provide extended controlled release of CHI therefrom after application to the particular field use.

The assay method used to determine the amount of CHI in these CHI/emulsifier/oxidized wax compositions in an in vitro bioassay with the sensitive yeast, *Saccharomyces pastorianus;* described by Whiffen (J. Bact. 56:283-291, (1948), and such assay has been adapted in studies to determine levels of CHI in various types of biological materials, see, e.g., Lemin, A. J., et al. (1960), "Translocation and Persistence of Cycloheximide (Actidione) in White Pines," 6, pp. 304-314, and (references 31 and 39). More recently, *S. cerevisiae* has been used in this bioassay. See Phelps, W. R., et al. (1967), "Translocation and Persistence in Eastern White Pine," Forest Sciences, 13, pp. 90-94. The latter yeast organism is sensitive to 0.02 parts per million CHI and is used routinely in assays in laboratories of The Upjohn Company. Cultures of *S. cerevisiae* and details on the bioassay are available on request.

CYCLOHEXIMIDE TURBIDIMETRIC ASSAY—SACCHAROMYCES CEREVISIAE UC1606

| Preparation of Cycloheximide Broth: (Single Strength) | |
|---|---|
| Dextrose | 20 g |
| Yeast | 5 g |
| Potassium phosphate monobasic | 2 g |
| Liver paste | 100 mg |
| Distilled water q.s. | 1000 ml |
| ph | 5.0 |

This medium is made up double strength and is diluted one-half at time of assay. Transfer the broth into flasks or bottles and autoclave 15 lbs. for fifteen minutes. This sterile medium may be stored in refrigerator up to four weeks.

Incolum

*Saccharomyces cerevisiae* UC10606 is maintained on slants of Sabouraud's Maltose Agar or suspended in Sabouraud's Liquid Medium and frozen in liquid nitrogen. Prepare 4 colony isolation plates using Sabouraud's Maltose Agar. Incubate for 18 to 36 hours at 32° to 37° C. or until discreet colonies may be selected. Transfer one colony to each of one or more slants of Sabouraud's Maltose Agar and incubate at 18 to 36 hours at 32° to 37° C. Using a freshly grown slant, wash with about 2 ml of Sabouraud's Liquid Medium and inoculate a Roux bottle of Sabouraud's Maltose Agar. Incubate 18 to 36 hours at 32° to 37° C. Wash the Roux bottle with two aliquots of about 10 ml each of Sabouraud's Liquid Medium. Pool three washes; this is the bulk inoculum. This suspension, prepared in quantity, may be dispensed into ampoules and frozen nitrogen for long-term storage. Or this suspension will last one week if refrigerated. To prepare the incolum for assay, add 0.1 ml of the bulk inoculum to a test tube containing 10 ml cycloheximide broth plux one 6 mm glass bead and shake in a water bath shaker overnight at 35° to 37° C. At the time of assay the Cycloheximide Broth is inoculated and approximately 2.2 percent of overnight culture suspension.

Standard Preparation

A stock solution of a suitable Cycloheximide Reference Standard is prepared in acetate buffer, pH 5, to a final concentration of 100 mcg per ml. This stock solution may be frozen and stored in gas-phase of liquid nitrogen. At the time of assay, dilute the stock solution to final concentrations of 0.1; 0.15; 0.2; 0.25; and 0.3 mcg of cycloheximide per ml with acetate buffer, pH 5.

CYCLOHEXIMIDE TURBIDIMETRIC ASSAYS—*SACCHAROMYCES CEREVISIAE* UC 10606

Sample Preparation

The samples of the various cycloheximide products are prepared according to existing sample preparation procedures and diluted to a final concentration of 0.2 mcg per ml with acetate buffer, pH.

Assay Preparation

Test tubes 22×175 mm are used. Prepare duplicate tubes for each of the five standard levels. Prepare 5 tubes of each sample. Pipette 1 ml of each standard solution into each of five tubes. Pipette 1 ml of sample solution into each of the five tubes. Add a 6 mm glass bead and 9 ml of inoculated Cycloheximide Broth to each tube. Prepare a blank of 1 ml acetate buffer, pH 5, and 9 ml of inoculated medium.

Incubation

The prepared tubes are placed in a shaking water bath at 35-37 C. for 4-5 hours. To the inoculated blank add 0.5 ml of formalin (25% formaldehyde of 37% Mallinckrodt No. 5016) immediately and incubate with other tubes 4-5 hours; the tubes are remeved and 0.5 ml of a 25% formaldehyde solution is added to each tube. Read the percent light transmission of the tubes on a suitable colorimeter using a wavelength of approximately 640 m.

Calculation

Construct a standard curve using the average percent transmittance (T) of each of the five standard levels and plotting on arithmetic graph paper. The ordinate is percent light transmission. The abscissa is cycloheximide concenntration. The response line is drawn either through these points by inspection or through points plotted for highest and lowest percent transmission values obtained by means of the following equations:

$$L = \frac{3a + 2b + c - e}{5} \quad H = \frac{3e + 2d + c - a}{5}$$

Note: A computer program may be used to fit the least squared line and calculate potencies.

CYCLOHEXIMIDE TURBIDIMETRIC ASSAY
*SACCHAROMYCES CEREVISIAE UC*1606 where,

L=Calculated transmission value for the lowest concentration of the standard response line.

H=Calculated transmission value for the highest concentration of the standard response line.

a,b,c,d,e=Average transmission values for each concentration of the standard response line, lowest to the highest, respectively.

One or more of the liquid CHI/emulsifier/oxidized wax melt compositions of this invention can be sprayed directly into a room temperature air container and cooled to prilled shape to obtain a mixed prilled composition having varied controlled release rates. Alternatively, one or more of the liquid CHI/emulsifier/oxidized melt compositions can be sprayed into inert, granular particles, preferably 4 to 40 mesh in size, and then cooled to a hard, solid granule so as to contain in the resulting, cooled CHI/emulsifier/oxidized wax/carrier granule from about 0.03 to about 2.0 percent, by weight, based on the weight of the total composition of cycloheximide (CHI), which can then be packaged, shipped, and used directly by the user by granular application methods to effect application of this controlled release form of CHI to cotton, grasses, and valuable grass-type crops.

The liquid melt compositions of this invention can also be sprayed onto objects or surfaces for use as a coating to control and reduce rodent populations.

This invention is further illustrated by the following detailed examples, which are intended only as being illustrations and not as being limitations of the invention.

Preparations 1 and 2

These examples describe my preferred methods for making or preparing the three component mixtures used in this invention:

1. Oxidized wax (Petranauba C);
2. Surfactant (Brij 78);
3. Cycleheximide (CHI).

The wax, 475 gm, is weighed and placed into a melting vessel which is maintained at about 100° C. (Range 190°-225° F.). The surfactant is weighed (25 gm) and added to the melted wax. A stirring device is used to produce a homogeneous mixture of wax and surfactant. The cycloheximide (CHI) is weighed (1.75 gm) and carefully added to the melt in a manner that will avoid producing lumps. However, variations on the weight ratios of the three ingredients vary widely for various applications.

The resulting mixture is stirred at a speed adequate to produce complete cycloheximide dispersion but not great enough to introduce any substantial amounts of air into the resulting melted mixture. A mixing time adequate to insure obtaining a homogeneous mixture is used.

Optionally, starch comprising up to about 30% of the wax-mixture by weight can be added as a fourth ingredient to the melting mixture as a diluent.

EXAMPLE 1

A hot melt spray unit such as a Nordson Model HM-IV is preheated to 100° C. The spray unit consists of a thermostatic individually controlled melt tank, a delivery hose and a spray gun. The selected hot homogeneous wax/surfactant/cycloheximide melt is poured into the 100° C. hot melt tank. The mixture is stirred and allowed to equilibrate. The spray gun nozzle is pointed up into the air at approximately a 45° angle from a height of about five feet from the bottom of a collection tank. The spray unit pump is started and the spray gun is activated, spraying hot melt composition into the air (ambient temperature in the collection area maintained at about 65° F.). The hot wax composition congeals before striking the collection area and forms substantially spherical beads or granules. The size of the beade can be varied by adjusting the spray unit's pump pressure and changing or adjusting the size of the nozzle tip. The congealed wax composition granules can be produced in a fairly narrow uniform size range. The granules are allowed to cool thoroughly before packaging. The granules are stored at room temperature away from direct sunlight.

EXAMPLE 2

After removing the stirring or agitation device from the selected melted oxidized wax/surfactant/cycloheximide composition, the composition is removed from the heat source and cooled at room temperature overnight. The resulting solidified oxidized wax composition is removed from its container and cooled to near dry ice temperatures (about −78° C.). The hardened wax composition is broken into small fragments or granules, first by manually reducing the size of the wax composition block with a hammer or similar device, followed by further size reduction using a blender or a Colton mechanical granulator, or similar device. The resulting wax composition granules are screened to the desired size (preferably 10–40 mesh) and stored as described above.

EXAMPLE 3

The granules described hereinbelow are not a blend of wax composition granules and clay granules but rather they are wax composition granules physically bonded to clay granules. However, due to premature congealing of the wax composition and/or destruction of the physical or chemical bond between the wax composition and the clay particles there may be a minor amount, say less than 10 percent by weight, of individual wax composition particles mixed with clay granules, but such is not the intent of this invention.

The selected wax/surfactant/cycloheximide composition is prepared as described above and poured into the preheated hot melt spray unit (described in Example 1 above). Clay granules of the desired size (30 to 60 mesh) are placed into a revolving pan or drum designed to effect a rolling action of the granule contents therein. The pan or drum is heated to maintain the granules therein within a temperature range of 130°-180° C. The pan or drum is rotated to effect rolling action on the clay granules while the hot wax composition is sprayed on the clay granules in such a manner as to produce clay granules coated with particles or droplets of congealed wax adhering to the clay. After the appropriate amount (about 5 to 20 weight percent) of wax composition has been sprayed onto and become bound to the clay granules contained in the rotating pan or drum, spraying is discontinued and the wax composition-coated clay granules are cooled, screened to appropriate (10 to 40 mesh) size and stored in a cool area out of direct sunlight.

EXAMPLE 4

This example illustrates typical control release formulations for use of the compositions of this invention:

A. For Prilling:

A hot melt mixed composition prepared as described in Preparation 1 containing approximately the following proportions:

(a) 0.03 percent w/w of cycloheximide, (range about 0.03 to 15 w/w percent);
(b) 5.0 percent w/w of Brij 78 ®, (range about 0.01 to 25 percent);
(c) 94.97 percent w/w of Petronauba ® C brand of oxidized wax, (range 45 to 99 percent);
(d) (optional) about 1 to about 30 percent w/w of starch as a diluent.

The melted mixture comprising the above components is sprayed to solidify the melted drops to solid prill form.

B. For a Wax Composition/Clay Granule:

A liquid melt of mixed composition, prepared as described in Preparation 1, containing approximately the following proportions:

(a) 0.15 percent w/w of cycloheximide, (range 0.15 to 30 percent);
(b) 3.0 percent w/w of Brij 78, (range 0.1 to 10 percent),
(c) 96.85 percent w/w of Petronauba ® C, (range 60 to 99.75 percent);

is sprayed onto Florex ® brand of agriculturally useful clay granules (30 to 60 mesh size, a total of 190 milliliters) of the liquid melt per kilogram of clay granules is applied. Upon cooling to hardness, the resulting cycloheximide/surfactant/wax/clay granules are tan-grayish in color, partially covered by an off-white hard wax coating of 10 to 40 mesh size.

EXAMPLE 5

Fine particles of the oxidized wax/emulsifier/CHI mixture can also be used for foliar application. These particles can be applied to the plant as a dust when mixed with a very fine diluent solid or as a dispersion in a surfactant-water mixture. The fine particles, e.g., 60 to 325 mesh, can be prepared by milling the congealed, oxidized wax-emulsifier-CHI or by spray congealing the melt at higher pressures or with different nozzles than those which are generally used for prill production. The proportion of ingredients for this application of the composition can be the same as those in Example 4B, ingredients (a), (b) and (c).

A line graph is provided to illustrate various possible use applications of the compositions of this invention

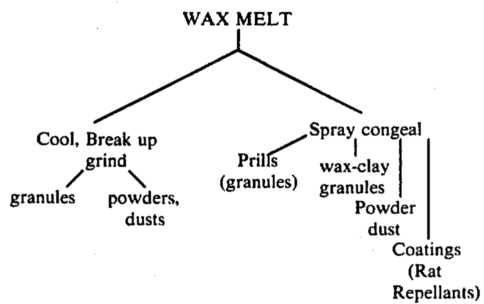

These new CHI/surfactant/oxidized wax compositions can be applied to soil by broadcast or banding application methods, at the rate of from about 5 to about 500 pounds per acre of soil or foliar surface in appropriate solid or liquid vehicle form to accomplish destruction or control of known agriculturally harmful fungi such as those which cause cherry leaf spot, wheat rust, bean anthracnase, rose powdery mildew, turf diseases (e.g., melting-out, fading out, and Pythium caused diseases) and the like. It is known, for example, that CHI will control the following specific fungus organisms:

| | |
|---|---|
| *Armillaria mellea* | 20 ppm CHI is a lethal dose |
| *Endoconidiophora fagacearum* | CHI fungislatic at 40 ppm; fungicidal at 200 ppm |
| *Fusarium lycopersci* | CHI completely inhibits at 100 ppm; moderate activity at 50 ppm |
| *Fusarium solani* | CHI completely inhibits at 500 ppm; partial inhibition at 100 ppm and lower |
| *Phytophthora cactorum* | CHI completely inhibits at 4 ppm |
| *Phytophthora cinnamomi* | CHI fungicidal at 5 ppm in dry soil; at 25 ppm in agar, and as soil drench |
| *Pythium deboryanum* | CHI completely inhibits growth at 4 ppm |
| *Rhizoctonia solani* | CHI inhibits at 50 ppm |
| *Sclerotium rolfsii* | CHI completely inhibits at 25 ppm; at 2.5 ppm in 72 hours |
| *Trichoderma viride* | CHI completely inhibits growth at 100 ppm; partial at 20 ppm |

and other fungi as well.

Various of these compositions can be blended together to obtain a spread of CHI treatment times, ranging from quick release (8 hours or less) to thirty days or more to protect seeds, seedlings and growing plants against fungi which are known to attack such plants during critical periods of their growth. For example, simple three component compositions of this invention of the same three ingredients can be altered to accomplish quick release (8 hours or less) or extended CHI retention (over 32 days). These components and proportions are:

| Formulation | Parts by Weight | | | |
|---|---|---|---|---|
| Components | 1 | 2 | 3 | 4 |
| Petronauba C | 12.0 | 13.4 | 14.25 | 14.7 |
| Brij 78 | 3.0 | 1.5 | .75 | .3 |
| (% surfactant) | (2.0) | (10) | (5) | (2) |
| Cycloheximide | .0525 | .0525 | .0525 | .0525 |

The actual weight of each formulation recovered from the mixing container will be somewhat less than the total of the above weights shown for each composition, depending upon the size of the container and the effort made to remove and collect all of the formulation. But if the components are uniformly blended to a homogeneous mixture, the proportions remain the same regardless of the weight recovered.

These formulations were tested by standard CHI aqueous test methods and found to release all or most of their CHI content as follows:

| Formulation | Time of Total Release |
|---|---|
| 1 | 8 hours |
| 2 | 48 hours |
| 3 | 16 days |
| 4 | over 32 days |

Other variations in release rates can be accomplished by using formulations which are mixtures of these compositions' different HLB rated surfactants or different proportions of surfactants, for given amounts of oxidized wax and cycloheximide contents.

Although cycloheximide (CHI) is the primary antibiotic active ingredient of these compositions, other known derivative forms of cycloheximide, such as the oxime, the acetate, the cycloheximide isomer, the cycloheximide semicarbazone, etc., can be used in place of CHI as the active antibiotic in these compositions which are to be used against fungus organisms known to be susceptible to treatment thereby. In PLANT DISEASE REPORTER, Vol. 42, No. 5, May 15, 1958, Ford/Klomparens/Hanna, in an article entitled "Cycloheximide (ActiDione®) and Its Agricultural Uses", review and summarize various publications and reports of the uses and inactivities of CHI against a variety of fungus organisms and situations. The compositions of this invention are intended for use primary for soil and turf applications and in fine dust and in oleaginous liquid suspension formulations to treat susceptible fungus infestations where a time release is desired for a critical time period.

I claim:

1. A composition useful for the controlled release of cycleheximide, which consisting essentially of a hardened, substantially uniform mixture of:

(a) from about 0.03 to 30 percent, by weight, of cycloheximide;

(b) from about 0.01 to 25 percent, by weight, of an emulsifier having an HLB number within the range of from about 5 and 18; and (c) from about 45 to 99 percent, by weight, of an oxidized wax which contains about 5 to about 17 pounds of oxygen per 100 pounds of wax, prepared by adding the cycloheximide (a) and emulsifier, (b) to the melted wax, (c) making a homogeneous mixture thhereof, and then cooling the resulting mixture to a solid form.

2. A composition according to claim 1 wherein the emulsifier is a non-ionic polyoxyethylene stearyl ether.

3. A composition according to claim 1 wherein the oxidized wax is an emulsifiable wax having a melting point of 190–200 F., an acid number of 22–28, and a saponification number of 50–60 containing about six units of oxygen per 100 units of wax.

4. A composition according to claim 1 wherein the oxidized wax is an oxidized polyethylene/$C_1$ to $C_4$-alkanol telemer having a molecular weight of from about 1000 to about 3000 containing from about 3 to about 9 percent of oxygen by weight, based upon the weight of the oxidized wax, and an acid number of not more than about 50.

5. A composition according to claim 1 sprayed in the liquid-melt state onto an inert carrier, granules of 10 to 40 mesh size so as to contain, in the resulting cooled, coated granule, from 0.03 to 6 percent by weight, based on the weight of the composition, of cycloheximide.

6. A composition according to claim 1 which further includes up to about 30 percent by weight of starch, based on the weight of the wax-emulsifier CHI mixtures.

* * * * *